United States Patent
Berlinger et al.

(10) Patent No.: US 10,297,042 B2
(45) Date of Patent: May 21, 2019

(54) MEDICAL IMAGE FUSION WITH REDUCED SEARCH SPACE

(71) Applicant: Brainlab AG, Munich (DE)

(72) Inventors: Kajetan Berlinger, Munich (DE); Hagen Kaiser, Icking (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/547,721

(22) PCT Filed: Jun. 29, 2016

(86) PCT No.: PCT/EP2016/065076
§ 371 (c)(1),
(2) Date: Jul. 31, 2017

(87) PCT Pub. No.: WO2017/001441
PCT Pub. Date: Jan. 5, 2017

(65) Prior Publication Data
US 2018/0047183 A1 Feb. 15, 2018

Related U.S. Application Data

(63) Continuation-in-part of application No. PCT/EP2015/064804, filed on Jun. 30, 2015.

(51) Int. Cl.
*G06T 7/73* (2017.01)
*A61B 6/00* (2006.01)
(Continued)

(52) U.S. Cl.
CPC .............. *G06T 7/74* (2017.01); *A61B 6/5229* (2013.01); *A61B 6/5235* (2013.01);
(Continued)

(58) Field of Classification Search
CPC .............. H04N 7/181; G06K 9/00771; G06K 2209/40; G06K 9/00369; G06K 9/4671;
(Continued)

(56) References Cited

U.S. PATENT DOCUMENTS 6,144,875 A   11/2000   Schweikard et al.
6,501,981 B1   12/2002   Schweikard et al.
(Continued)

FOREIGN PATENT DOCUMENTS

WO   WO2015127870 A1   9/2015

OTHER PUBLICATIONS

International Search Report and Written Opinion for PCT/EP2016/065076 dated Feb. 8, 2016.
(Continued)

*Primary Examiner* — Aklilu K Woldemariam
(74) *Attorney, Agent, or Firm* — Middleton Reutlinger

(57) ABSTRACT

A computer implemented method for performing fusion of 3D image data, which represent at least a part of a patient's body, with two 2D images of the patient's body with a known spatial relation between the viewing directions of the 2D images, comprising the steps of: —acquiring the 3D image data, —acquiring the two 2D images, —calculating two virtual images from the 3D image data, the two virtual images corresponding to the two 2D images, —classifying the two 2D images into a primary and a secondary image, —determining a primary alignment between the primary image and the corresponding virtual image such that they match, —calculating a spatial axis relative to the viewing directions of the two 2D images from the primary alignment and a predetermined point which is imaged in the virtual image which corresponds to the primary image, wherein the spatial axis is a line in space on which the predetermined point lies, and —performing fusion of the 3D image data with the two 2D images based on the calculated spatial axis in order to obtain a virtual position of the 3D image data in space.

17 Claims, 3 Drawing Sheets

(51) Int. Cl.
*G06T 7/33* (2017.01)
*A61N 5/10* (2006.01)
*G06T 19/20* (2011.01)
*A61B 6/04* (2006.01)

(52) U.S. Cl.
CPC ......... *A61N 5/1039* (2013.01); *A61N 5/1049* (2013.01); *G06T 7/33* (2017.01); *G06T 19/20* (2013.01); *A61B 6/0407* (2013.01); *A61B 6/4085* (2013.01); *A61N 5/103* (2013.01); *A61N 2005/1062* (2013.01); *G06T 2207/10004* (2013.01); *G06T 2207/10081* (2013.01); *G06T 2207/10116* (2013.01); *G06T 2207/20092* (2013.01); *G06T 2207/20221* (2013.01); *G06T 2207/30004* (2013.01); *G06T 2207/30168* (2013.01); *G06T 2210/41* (2013.01); *G06T 2219/2004* (2013.01); *G06T 2219/2016* (2013.01)

(58) Field of Classification Search
CPC .............. G06K 9/6269; G06K 9/00342; G06T 2207/30196; G06T 2207/30232; G06T 7/292; G06T 7/564; G06T 7/77; G06T 7/2093; G06T 15/205; G06T 7/0012; G06T 7/62; G06T 2207/10136; G06T 2207/20061; G06T 2207/30004; G06T 2207/30044; G06T 7/12; G06T 7/143; G06T 7/155; G06T 2207/10132; G06T 7/11; G06T 2207/10048; G06T 2207/30088; G06T 2207/10021; G06T 7/0028; G06T 7/33; G06T 7/38; G06T 7/50; G06T 7/55; G06T 19/20; G06T 2207/10004; G06T 2207/10081; G06T 2207/10116; G06T 2207/20092; G06T 2207/20221; G06T 2207/30168; G06T 2210/41; A61N 2005/1061; A61N 5/1049; A61N 5/1067; A61N 2005/1062; A61N 5/107; A61N 7/02; A61N 2005/1054; A61N 2005/1058; A61N 5/1037; A61N 5/1039; A61N 5/1077; A61N 5/01; A61N 5/10; A61N 5/1069; A61B 5/1127; A61B 6/5217; A61B 6/541; A61B 2034/105; A61B 5/062; A61B 2090/392; A61B 2562/0233; A61B 5/1075; A61B 5/1128; A61B 6/4258; A61B 6/4417; A61B 6/469; A61B 2034/302; A61B 2090/36
USPC ........ 382/103, 123, 173, 293; 600/427, 429, 600/431
See application file for complete search history.

(56) References Cited

U.S. PATENT DOCUMENTS

| | | | |
|---|---|---|---|
| 6,516,046 B1 | 2/2003 | Frohlich et al. | |
| 7,277,118 B2* | 10/2007 | Foote | G06T 3/4038 348/218.1 |
| 8,160,676 B2* | 4/2012 | Gielen | A61B 5/06 382/128 |
| 8,160,677 B2* | 4/2012 | Gielen | G06K 9/3216 382/128 |
| 8,948,471 B2* | 2/2015 | Fichtinger | A61B 6/504 382/128 |
| 2004/0127796 A1* | 7/2004 | Chalana | A61B 5/204 600/449 |
| 2005/0043614 A1* | 2/2005 | Huizenga | A61B 5/055 600/427 |
| 2005/0059887 A1 | 3/2005 | Mostafavi et al. | |
| 2005/0251039 A1* | 11/2005 | Chalana | A61B 5/204 600/437 |
| 2006/0074304 A1* | 4/2006 | Sayeh | A61B 5/1127 600/427 |
| 2006/0235301 A1* | 10/2006 | Chalana | A61B 5/204 600/443 |
| 2006/0269165 A1 | 11/2006 | Viswanathan | |
| 2007/0238952 A1* | 10/2007 | Boese | G06T 7/38 600/407 |
| 2008/0037843 A1 | 2/2008 | Fu et al. | |
| 2011/0080466 A1* | 4/2011 | Kask | G06T 5/006 348/43 |
| 2012/0044476 A1* | 2/2012 | Earhart | G01S 3/7867 356/4.01 |
| 2012/0109608 A1 | 5/2012 | Core et al. | |
| 2013/0060132 A1* | 3/2013 | Liao | A61B 6/12 600/431 |
| 2014/0073907 A1* | 3/2014 | Kumar | A61B 10/00 600/414 |
| 2014/0228707 A1* | 8/2014 | Brieu | A61B 5/00 600/567 |
| 2015/0190200 A1* | 7/2015 | Courtine | A61N 1/36003 604/20 |
| 2015/0269427 A1* | 9/2015 | Kim | G06K 9/00369 348/159 |
| 2015/0287194 A1* | 10/2015 | Schoenmeyer | G06T 7/0012 382/128 |
| 2015/0294483 A1* | 10/2015 | Wells | H04N 7/181 382/103 |

OTHER PUBLICATIONS

Schweikard, et al. "Respiration Tracking in Radiosurgery without Fiducials" Int J Medical Robotics and Computer Assisted Surgery pp. 19-27. 2005.

Junlin, et al. "The Registration of 2D/3D Images in Robot-Assisted Cervical Disc Replacement Surgery", International Conferences of Complex Medical Engineering, May 25-28, Beijing, China.

* cited by examiner

MEDICAL IMAGE FUSION WITH REDUCED SEARCH SPACE

TECHNICAL FIELD

The present invention relates to a computer implemented method for performing fusion of 3D image data, which represent at least a part of a patient's body, with two 2D images of the patient's body with a known spatial relation between the viewing directions of the 2D images and to a corresponding computer program and system.

DESCRIPTION

Many medical applications and systems require a fusion of 3D image data with one or more 2D images. The 3D image data represent and object and/or a part of a patient's body and typically is image data obtained using a suitable imaging modality, such as CT (computed tomography), MRI (magnetic resonance imaging), ultrasound imaging or the like. In the following, the term "patient" is used as a synonym for the expression "part of a patient" as long as no distinction has to be made. The 2D images represent the same object and/or part of a patient and are typically obtained using a suitable imaging modality, such as x-ray imaging or ultrasound imaging. One or more of the 2D images can be captured using an EPID (electronic portal imaging device) which utilizes a treatment beam as a beam source. The 2D images are typically captured during or shortly before a medical treatment and therefore represent the current position of the object and/or patient relative to the imaging system(s) used for capturing the 2D image(s). The 3D image data is typically captured in a treatment phase and is therefore older than the 2D images.

One exemplary application of the fusion is to derive the current position of the object and/or patient relative to the imaging system(s). This is achieved by virtually positioning the 3D image data relative to the imaging system(s) such that virtual images calculated from the 3D image data match the 2D images as good as possible. A virtual image is calculated from the 3D image data for an assumed viewing direction in space which equals the viewing direction of the corresponding imaging systems which were used for capturing the corresponding 2D image. The calculation of virtual images from 3D image data is well known, for example as so-called DRRs (digitally reconstructed radiographs) from CT image data. Suitable algorithms are also known for other modalities of the 3D image data. The modalities of the 2D images and the virtual images are typically the same, such that for example the virtual image is a DRR and the 2D image is an x-ray image. This includes taking the beam energy into account in order to mimic the properties of the imaging system, for example if one 2D image was captured by an EPID with a MV beam and one 2D image was captured by an x-ray imaging system with a kV beam. However, it is also possible to mix the modalities.

A very specific application is radiosurgery or radiotherapy in which a tumor in the patient's body is to be treated. The patient has to be aligned relative to a treatment beam generator such that the tumor lies in the isocenter of the treatment beam generator.

Once the virtual images and the corresponding 2D images match as good as possible, it can be assumed that the virtual position of the 3D image data (relative to the imaging systems) corresponds to the current position of the patient (relative to the imaging systems). In this document, the term "position" means the location in up to three translational dimensions and the orientation in up to three rotational dimensions. A (virtual) position is thus a combination of a (virtual) location and a (virtual) orientation.

The basic approach for finding the virtual position of the 3D image data is a brute force approach which tests a large number of virtual positions (in six dimensions) and selects the best one among those virtual positions. However, this requires a lot of computational power, such that different optimized search strategies have been employed. This document discloses another approach which reduces the computational complexity of an automatic fusion or provides guidance to a user in a (partly) fusion.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a computer implemented method for performing fusion of 3D image data, which represent at least a part of a patient's body, with two 2D images of the patient's body with a known spatial relation between the viewing directions of the 2D images. A viewing direction of a 2D image is the direction with which an imaging system used for obtaining the 2D image looks onto the patient's body. If the 2D image is an optical image, then the viewing direction typically is the optical axis of the camera comprised in the imaging system. If the 2D image is an x-ray image, the x-ray imaging system typically utilizes a cone-beam type x-ray. The viewing direction of the x-ray image is then the central axis of the cone-beam.

The method comprises the steps of acquiring the 3D image data and of acquiring the two 2D images. The 3D image data is typically represented by a 3D image data set and a 2D image is typically represented by a 2D image data set. The 3D image data can be generated by an imaging system having a suitable modality, such as CT, MRI or ultrasound. The 2D images can be captured by one or more imaging systems having a suitable modality, such as x-ray or ultrasound. A single 2D imaging system can be used for consecutively capturing the two 2D images, or two 2D imaging systems can be used, which allows to capture the two 2D images simultaneously.

Preferably, the modalities used for capturing the 3D image and the two 2D images are the same.

The method further involves the step of calculating two virtual images from the 3D image data, the two virtual images corresponding to the two 2D images. There are thus two image pairs, each pair comprising a virtual image and a corresponding 2D image. The spatial relation between the viewing directions of the virtual images is for example identical to the spatial relation between the viewing directions of the 2D images. In one embodiment, the viewing directions of the virtual image and the corresponding 2D image which constitute a pair of images are identical. It shall be noted that the two 2D images are real images of the patient's body, while the virtual images are synthesized from the 3D image data and are therefore virtual images.

Algorithms for calculating virtual images from 3D image data are known for different modalities of the 3D image.

Taking CT data as an example for 3D image data, algorithms for calculating so-called DRRs (Digitally Reconstructed Radiographs) are known in the art. A virtual x-ray beam is sent through the 3D image data and the DRR represents the attenuation of the beam on its way through the 3D image data.

The method further comprises the step of classifying the two 2D images into a primary image and a secondary image. The primary image can also be referred to as "good image" and the secondary image can be referred to as "bad image". A good image represents information which is evaluable more easily than the information comprised in the bad image. In the following, the virtual image corresponding to the primary image is referred to as primary virtual image, and the virtual image corresponding to the secondary image is referred to as secondary virtual image.

The method further involves the step of determining a primary alignment between the primary image and the corresponding virtual image such that they match. This does for example mean to move the primary image and the corresponding virtual image relative to each other such that they coincide as good as possible. In other words, a similarity measure value indicating the similarity between the primary image and the corresponding virtual image is maximized for the primary alignment. Since the primary image is a "good image", the primary alignment can typically be found reliably.

Determining the primary alignment can be performed manually or automatically. If the primary alignment is determined automatically, a suitable algorithm is used for finding a relative position between the primary image and the primary virtual image such that the best match is achieved. If the primary alignment is determined manually, a user input is received for manually aligning the primary image with the primary virtual image. The user input for example represents a shift in two translational dimensions along the plane of the images.

Since typically a serious amount of time passes between capturing of the 3D image data and capturing of the two 2D images, the internal structure of the patient's body has likely changed during this period of time, which means that the virtual images do not exactly match the corresponding 2D images. For example, an organ or an object, such as a tumor, has moved within the patient's body and is thus imaged at different locations relative to other structures like bones.

The method further involves the step of calculating a spatial axis relative to the viewing directions of the two 2D images from the primary alignment and a predetermined point which is imaged in the virtual image which corresponds to the primary image, i.e. in the primary virtual image, wherein the spatial axis is a line in space on which the predetermined point lies. For each pixel of a 2D image captured by a 2D imaging system, there is a corresponding line in space which depends on the properties of the imaging system. A point which is imaged in a particular pixel must lie on this corresponding line in space.

The spatial axis is a line in space which corresponds to a particular pixel of the primary image. The particular pixel is a pixel at a location in the primary image at which a particular pixel of the primary virtual image is located if the alignment between the primary image and the primary virtual image is the primary alignment. The particular pixel in the primary virtual image is for example a pixel in the center of the primary virtual image. In another example, the particular pixel in the primary virtual image is a pixel which represents a predetermined point in the 3D image data, such as for example a point in an organ or an object such as a tumor. In a very specific example, the predetermined point is the center of a tumor represented by the 3D image data. In this particular case, the primary alignment preferably means that the primary image and the primary virtual image are shifted relative to each other such that the tumor imaged in the two images is congruent. The pixel of the primary image which shows the center of the tumor is then identified and the spatial axis on which the center of the tumor lies is calculated.

As outlined above, the spatial axis can be calculated from the particular pixel in the primary image and the properties of the imaging system which was used for capturing the primary image. The spatial axis has a particular position relative to the viewing directions of the two 2D images.

The method further involves the step of performing fusion of the 3D image data with the two 2D images based on the calculated spatial axis in order to obtain a virtual position of the 3D image data in space. As explained above, the primary image is a "good" image such that the primary alignment is typically reliable. This means that the virtual location of the 3D image data in a plane which is perpendicular to the calculated spatial axis is determined reliably by the primary alignment. The missing component of the virtual location of the 3D image data in space is thus basically along the spatial axis. This component can then be determined by the fusion, for example by determining a secondary alignment between the secondary image and the secondary virtual image, wherein the secondary alignment can be reduced to a shift along a line which is a projection of the spatial axis into the primary (virtual) image.

In other words, the two pairs of a 2D image and a virtual image are not analyzed independently of each other, but in a joint manner. In a first step, the primary image is used to determine a spatial axis along which the virtual location of the 3D image data is determined from the secondary image.

In one embodiment, the classification of the two 2D images into a primary image and a secondary image depends on the visibility of an object in the two 2D images. An example of the object is a tumor. The visibility of an object depends on the presence and position of other matter. Taking x-ray images as examples for the two 2D images, the visibility of a tumor in a 2D image is good if there are no disturbing objects, such as bones, in the path of the x-ray beam. The visibility of an object is typically better in one of the images, such that the 2D image with the better visibility is classified as the primary image and the other 2D image is classified as a secondary image.

In one embodiment, the classification is based on at least one of histograms of the two 2D images and the structure of the 3D image data along the rays used for calculating the virtual images corresponding to the two 2D images.

In one embodiment, a 2D image captured by an EPID is classified as a secondary image and a 2D image captured by an x-ray imaging system is classified as a primary image.

The 2D images are typically grayscale images. A histogram of a 2D image therefore reflects how often the possible gray values occur in the 2D image. The visibility of an object in a 2D image is typically good if there are at least two distinct ranges of gray values which occur significantly more often than the average.

If a virtual image is calculated from the 3D image data, a plurality of rays is typically placed through the 3D image data and the 3D image data is analyzed along each of those rays. In this case, rays which pass through the object can be identified. It can then be determined if there are any disturbing objects in the 3D data along said rays. If a majority or all of the rays which pass through the object do not pass through one or more disturbing objects, the visibility of the object in the virtual image will be good, such that it can be assumed that the visibility of the object in the corresponding 2D image is also good, thus making this 2D image a primary image.

In one embodiment, the fusion step involves a partly manual fusion. The partly manual fusion comprises the step of projecting the spatial axis into the secondary image in order to obtain an epipolar line in the secondary image. If the 3D image data is shifted along the spatial axis, the secondary virtual image is shifted along the epipolar line because it is a projection into the plane of the secondary image. In this document, the expression "partly manual fusion" is used instead of "at least partly manual fusion" for the sake of brevity. It can thus mean a partly or fully manual fusion.

The partly manual fusion further comprises the step of receiving user input for manually aligning the secondary image and the corresponding virtual image along the epipolar line only, thus obtaining a secondary alignment. This means that the user can shift the secondary virtual image relative to the secondary image only along the epipolar line, and a shift perpendicular to this line is prohibited. Such a shift would mean a shift of the 3D image data in a plane perpendicular to the spatial axis, which is undesirable because it is assumed that the location in this plane is correctly determined by the primary alignment. In this document, the statement that a shift, movement or change in position does not occur in a direction perpendicular to the spatial axis means that is has no component in such a direction.

The partly manual fusion further comprises the step of obtaining the virtual position of the 3D image data from the first alignment and the second alignment. In other words, the location of the 3D image data in a plane perpendicular to the spatial axis is determined from the first alignment and the virtual location of the 3D image data along the spatial axis is determined from the second alignment.

In this embodiment, the primary alignment is for example determined manually by receiving user input for manually aligning the primary image and the primary virtual image by shifting those two images relative to each other along the imaging plane. The user therefore first determines a primary alignment in the good image and subsequently the secondary alignment from the bad image, wherein the secondary alignment is limited to a linear shift which is restricted by the primary alignment and the spatial axis, and therefore the epipolar line in the second image, resulting therefrom.

In this embodiment, an object can be found or identified in both the primary image and the secondary image. In the primary image, the object is found by aligning a virtual image of the object with the primary image in two translational dimensions. The object is found or identified in the secondary image by shifting a virtual image of the object relative to the secondary image along the epipolar line only. The user is therefore guided to find or identify the object in the secondary image only at consistent locations.

In one embodiment, the partly manual fusion further comprises the step of displaying an overlay of the primary image with the corresponding virtual image according to the primary alignment and an overlay of the secondary image with the corresponding virtual image according to the secondary alignment. So once the user input is received for the secondary alignment, the two overlays are displayed such that the user can visually verify the primary alignment and the secondary alignment. When user input is received for the primary alignment, an overlay of the primary image and the primary virtual image can be displayed in a similar fashion.

It shall be noted that the overlays can be displayed in real time while the user input is received, thus allowing the user to verify the primary alignment and the secondary alignment in real time.

The viewing directions of the 2D images are typically not parallel to each other. This means that a shift of the 3D image data along the spatial axis means that the primary virtual image becomes smaller or larger as the 3D image data shifts along the spatial axis. This means that the user input for the secondary alignment results in a zoom of the primary virtual image, such that the user can judge the size of the primary virtual image for making his input regarding the secondary alignment in addition to identifying a match between the secondary image and the secondary virtual image. If the spatial axis is not parallel to the image plane of the second image, then a movement of the secondary virtual image along the epipolar line means a component of the virtual movement of the 3D image data in a direction perpendicular to the image plane of the secondary image. This means that the user input for the secondary alignment further results in a zoom of the secondary virtual image In this embodiment, and also the other embodiments, an initial virtual position of the 3D image data can be a starting point for the fusion. The virtual position of the 3D image data is amended starting from the initial virtual position. The initial virtual position is for example obtained by an initial fusion step of the 3D image data with the two 2D images or two initial 2D images. This initial fusion for example fuses bone structures in the 3D image data to bone structures imaged by the two (initial) 2D images, while the fusion based on the calculated spatial axis does, for example, focus on soft tissue imaged by the 3D image data and the two 2D images.

The initial virtual orientation of the 3D image data may be maintained as the virtual orientation of the 3D image data during the fusion. However, the virtual orientation can be adapted. In the case of a partly manual fusion, the virtual orientation can be adapted automatically or by receiving a user input.

In one embodiment, the two virtual images are calculated from the whole 3D image data. In another embodiment, the two virtual images are calculated from a subset of the 3D image data only, such as only the subset of the 3D image data which comprises a volume of interest or a particular object, such as a tumor. In this case, the virtual images basically represent the object only, such that the primary alignment, and also the secondary alignment, focuses on the object.

In one embodiment, performing fusion of the 3D image data with the two 2D images based on the calculated spatial axis means an automatic fusion which allows a translational shift of the 3D image data only along the spatial axis, wherein a shift is defined with respect to an initial virtual position of the 3D image data.

In the present embodiment, the virtual location of the 3D image data can only be adapted along the spatial axis, but not in any direction perpendicular to the spatial axis. Two components of the virtual location of the 3D image data are therefore fixed based on the primary alignment, wherein the third component of the virtual location of the 3D image data is calculated from the secondary image and the secondary virtual image.

In this embodiment, and all other embodiments related to an automatic fusion, this automatic fusion might also comprise an adaption of the rotational alignment of the 3D image data.

In one embodiment, performing fusion of the 3D image data with the two 2D images based on the calculated spatial axis involves that a translational shift of the 3D image data along the spatial axis is penalized less than a translational shift of the 3D image data in a direction perpendicular to the spatial axis, wherein a shift is defined with respect to an initial virtual position of the 3D image data.

In this embodiment, a translational shift of the 3D image data in a direction perpendicular to the spatial axis is not completely excluded as in the previous embodiment, but is impeded by the penalty. In other words, a translational shift perpendicular to the spatial axis is possible in a small degree if this leads to a far better match of the secondary virtual image with the secondary image.

As explained above, a typical approach for an automatic fusion is to calculate a similarity measure value which represents the similarity between a virtual image and a corresponding 2D image. However, this similarity measure can be modified by a penalty or penalty factor which introduces a boundary condition. This is used to bias the fusion, for example towards a particular virtual position or range of virtual positions.

In one embodiment, performing fusion of the 3D image data with the two 2D images based on the calculated spatial axis involves that a translational shift of the 3D image data along the spatial axis has a step width which is smaller than a step width of a translational shift of the 3D image data in a direction perpendicular to the spatial axis, wherein a shift is defined with respect to an initial virtual position of the 3D image data.

The initial virtual position of the 3D image data is supposed to be identical or close to the actual virtual position of the 3D image data. As outlined above, an approach is to calculate similarity measure values for a plurality of test virtual positions in order to determine the test virtual position which results in the highest similarity measure value. The test virtual positions are typically arranged with equidistant translational and/or rotational distances, thus resulting in a constant step width between the test virtual positions. Due to the different step widths along the spatial axis and the other axes, it is therefore unlikely that a test virtual position, which is shifted relative to the initial virtual position in a direction perpendicular to the spatial axis, results in a similarity measure value which is higher than a similarity measure value for a test virtual position which is not shifted relative to the initial virtual position in a direction perpendicular to the spatial axis.

In one embodiment, the 3D image data represent an object in or on the patient's body and the predetermined point is a point in the object. As explained above, the object is for example an organ or a tumor. The fusion might then concentrate on the object and neglect some or all parts of the 3D image data which do not represent the object.

In one embodiment, the method further comprises the step of calculating an offset which represents the difference between an initial virtual position of the object before the fusion and the virtual position of the object after the fusion. If the initial virtual position is determined by an initial fusion as explained above, it can be assumed that the patient is correctly positioned relative to the treatment beam generator, and therefore relative to the imaging system(s) used for capturing the two 2D images. However, the position of the object within the patient's body can have changed between the time at which the 3D image data has been captured and the time at which the two 2D images are captured. The offset then represents the displacement of the object within the patient's body between those two points in time.

In one embodiment, the method further comprises the step of dividing the offset into components along and/or around body axes of the patient and of comparing at least one of the components with a reference value. The dividing step means that, in a case of the offset being defined in three translational and three rotational dimensions, the offset is decomposed into components defined with reference to the body axes. Those body axes typically correspond to the superior-inferior-direction, the anterior-posterior-direction and the lateral direction. The offset is therefore transferred from a machine reference to a patient reference.

If it is asserted in the comparing step that the compared component exceeds the reference value, an indication signal can be output. This indication signal is a warning that the component is above the reference value. This allows to indicate suspicious offsets.

The reference value can be a predetermined value or a value which is calculated based on boundary conditions, such as object information regarding properties of the object. Those properties can for example be the type of object, such as tumor or not, and/or the position of the object in the patient's body. The position of the object in the patient's body may indicate predominant directions of movement of the object within the patient, for example due to a breathing activity.

In one embodiment, three reference values for the three body axes of the patient are determined depending on the object information. The ratios of the reference values then depend on the object information, in particular the position of the object within the patient's body. In this case, the components of the offset in the three directions corresponding to the body axes are for example not compared with absolute reference values, but with the ratios of the reference values in order to determine whether or not the offset is along a preferred direction.

In one embodiment, the method further comprises tracking of the object by repeating the steps of acquiring the two 2D images, determining a primary alignment, calculating a spatial axis and performing a fusion. The fusion is thus repeated for a sequence of 2D images over time, thus resulting in a sequence of virtual positions of the 3D image data over time. The position of the object can therefore be tracked, for example during a breathing activity of the patient. Tracking may also optionally involve repeating the step of classifying the two 2D images into a primary and a secondary image.

In one embodiment, the two 2D images are captured consecutively with the primary image being captured before the secondary image. In one implementation, the two 2D images are classified once into a primary image and a secondary image and it is considered that all subsequent 2D images having the same viewing direction as the first primary image are also primary images in the subsequent pairs of 2D images. In another implementation, each new pair of two 2D images is classified into a primary image and a secondary image and this classification is used as the order in which the next pair of 2D images is captured.

In one embodiment, the time elapsed between capturing the primary image and the secondary image of a pair of two 2D images is shorter than the time elapsed between capturing the secondary image of one pair of 2D images and capturing the primary image of the subsequent pair of 2D images. In this case, it can be assumed that the movement of the object within the patient's body is neglectable between capturing the primary image and the secondary image of a pair of 2D images. If the two 2D images are not captured simultaneously, it might be advantageous to allow a translational shift of the 3D image data perpendicular to the spatial axis, for example as described in the embodiments assigning a penalty to such a shift or using different step widths. This can compensate a movement of an object within the patient's body in the period between capturing of the two 2D images.

In this embodiment, the primary alignment can already be determined even if the secondary image has not been captured yet.

Once the fusion of the 3D image data with the two 2D images has been performed, tracking can be reduced to finding the object in another pair of 2D images, which is also referred to as current pair of 2D images or pair of current 2D images. Finding an object implies finding the location of the object in a 2D image. In this case, finding the object in a 2D image can be performed freely over both 2D images or using the epipolar approach. In the epipolar approach, the object is first found in the primary 2D image, and the object is then found in the secondary 2D image along the epipolar line as explained above.

In one embodiment, the location of the object in at least one of the two 2D images undergoes a plausibility check. In this check, a location is compared to the locations of the object in a preceding 2D image or with a trajectory of the locations in a plurality of preceding 2D images. If the found location in a 2D image is not plausible, then this 2D image is not classified as the primary image. If the locations of the object in both 2D images of the image pair is determined, the found location in one of the 2D images is plausible and the location in the other 2D image is not, then the 2D image for which the location is plausible is classified as the primary 2D image and the other 2D image as the secondary 2D image.

A trajectory can be a set of locations of the object in a set of 2D images which were captured using the same imaging device. In a more general embodiment, there is only one 3D trajectory, which is the trajectory of the predetermined point in space. This 3D trajectory is for example formed by the points in space that are defined by the locations of the object in preceding pairs of 2D images. As explained above, there is a spatial line for each pixel of a 2D image on which a point imaged by this pixel lies. If the spatial lines are determined for the locations of the object in both 2D images in a pair of 2D images, then the intersection of the spatial axes defines the spatial location of a point on the 3D trajectory. The 3D trajectory can be projected into a 2D image to obtain the trajectory. This can for example compensate a rotation of the object relative to the imaging devices.

In an alternative, the trajectory can also be determined from the 3D image data, in particular if the 3D image data is recorded for several points in time and thus reflects the movement of the object.

In the plausibility check, the distance of the found location of the object to the trajectory is calculated. This distance is compared to a threshold. If it is below the threshold, then the found location is plausible, otherwise it is not plausible.

In one embodiment, the distance is determined by calculating the distances between all points on the trajectory, that is all previously found locations that form the trajectory, and the found location in the current 2D image. Then the smallest out of those distances is determined and compared to the threshold.

In an alternative, a best-fit curve is calculated from the locations that form the trajectory. The distance is then the distance of the found location in the current 2D image to the best-fit curve. This is computationally less expensive, since the best-fit curve only has to be calculated once and calculating the distance between a curve and a point is a well-known mathematical task.

In one embodiment, the best-fit curve is a segment of a regression line. The regression line is calculated from the locations that form the trajectory. The segment of the regression line is limited by the two outermost locations out of the locations that were the basis for calculating the regression line. The segment of the regression line can optionally be extended at one or both of its ends by a particular amount. This particular amount can be different at the two ends. This extension allows plausible exceedances of the trajectory. If the trajectory does for example reflect a regular breathing activity, then the extension of the segment makes a location of the object for a deep inhale or exhale plausible.

In one embodiment, the best-fit curve is comprised of two splines. One of the splines corresponds to the locations of the object in one direction of the trajectory, such as an inhale action, and the other spline corresponds to the locations of the object in another direction of the trajectory, such as an exhale action. Those two splines intersect each other at the reversal points of the trajectory.

The best-fit curve can consist of the segments of the two splines between their two intersection points. Optionally, the best-fit curve can additionally comprise one or two extensions at the intersection points. An extension can be a line segment of the line which passes through the two intersection points. The extension for example starts at the intersection point and extends outwards for a predetermined amount. This predetermined amount can be different for two extensions of the best-fit curve.

The plausibility check may involve a temporal component. Since a trajectory of the object is typically caused by a repeated movement, such as a breathing cycle, the trajectory also defines a temporal order of the locations of the object. So if the found location is on (or close enough to) the trajectory, but on an unexpected position for the point in time at which the 2D image was captured, the location can nevertheless fail the plausibility check.

It shall be noted that the method can also be applied for performing fusion of 3D image data with more than 2D images. The more than two 2D images are classified into one or more primary images and one or more secondary images, such that each of the 2D images is either a primary image or a secondary image. Then a primary alignment is determined for each of the primary images and spatial axes are calculated for each primary alignment. The fusion is then performed based on the plurality of spatial axes.

The present invention further relates to a program which, when running on a computer, causes the computer to perform the method steps described herein. It also relates to a program storage medium on which the program is stored.

The present invention further relates to a system for performing fusion of 3D image data, which represent at least a part of a patient's body, with two 2D images of the patient's body with a known spatial relation between the viewing directions of the 2D images. The system comprises at least one imaging system for capturing the two 2D images and a computer on which the aforementioned program is stored and/or run.

DEFINITIONS

The method in accordance with the invention is for example a computer implemented method. For example, all the steps or merely some of the steps (i.e. less than the total number of steps) of the method in accordance with the invention can be executed by a computer. An embodiment of the computer implemented method is a use of the computer for performing a data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_v-mat.php and http://www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The present invention can for example be used with the ExacTrac® system or the Vero® system of the applicant in order to position a patient or to track a tumor within the patient.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
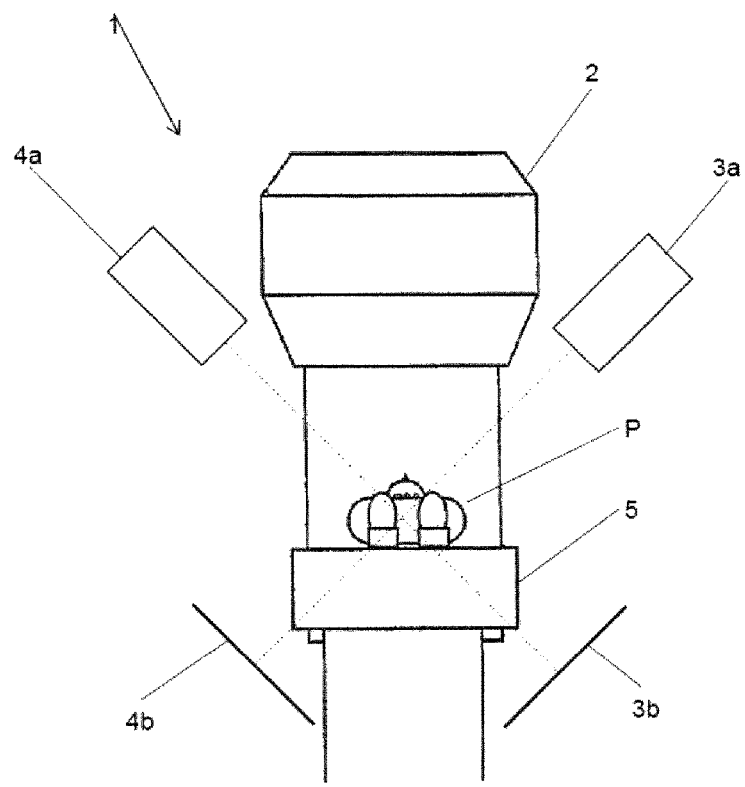
FIG. 1 a radiotherapy system,
FIG. 2 principles of the epipolar geometry,
FIG. 3 examples of two 2D images and corresponding virtual images, and
FIG. 4 a schematic system overview.

FIG. 1 shows an exemplary geometric arrangement of a radiotherapy system on which the present invention can be embodied. The system 1 comprises a treatment beam generator 2 which can generate a treatment beam for treating a tumor in a patient P. The system 1 further comprises two x-ray imaging systems 3 and 4. The x-ray imaging system 3 comprises an x-ray generator 3a and x-ray detector 3b. In analogy, the x-ray imaging system 4 comprises an x-ray generator 4a and an x-ray detector 4b. Each x-ray generator 3a, 4a generates a cone-shaped x-ray beam which passes through at least a part of the patient P before it hits the corresponding detector 3b, 4b. The axis of symmetry of the cone-shaped x-ray beam is referred to as the viewing direction of the imaging system 3, 4, and thus as the viewing direction of the x-ray images captured using the respective x-ray imaging system 3, 4. The viewing directions of the x-ray imaging systems are shown by dotted lines.

The patient P is located on a couch 5, wherein the couch 5 can be moved relative to the treatment beam generator 2 and the x-ray imaging systems 3 and 4.

The spatial relation between the x-ray imaging systems 3, 4, and therefore between their viewing directions, is known. The treatment beam generator 2 is rotatable about an axis which is orthogonal to the paper plane. During rotation of the treatment beam generator 2, the treatment beam always passes through a particular point in space, which is referred to as the isocenter of the treatment beam generator 2. This isocenter has a known location relative to the x-ray imaging systems 3 and 4.

Figure 2:
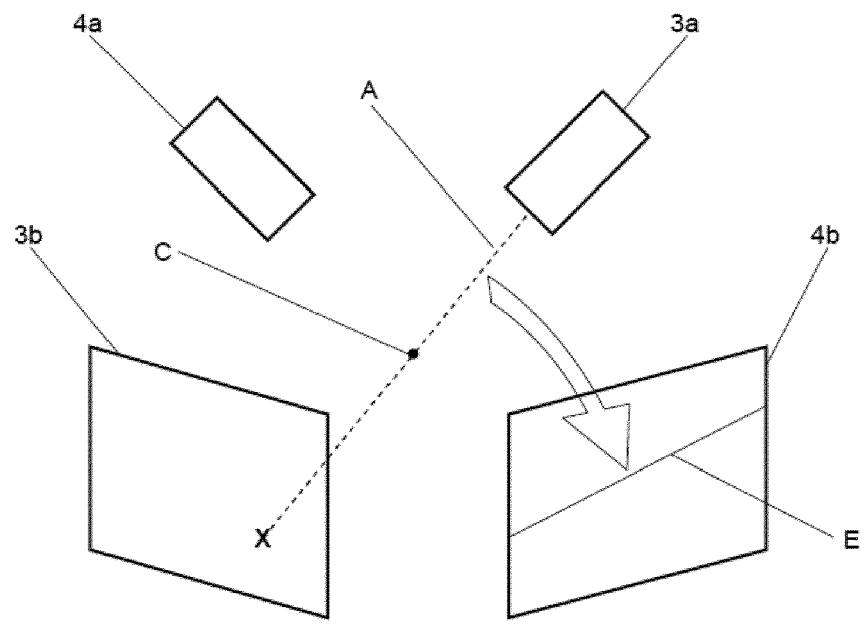

FIG. 2 schematically shows the basics of epipolar geometry. As can be seen from FIG. 2, a particular point C in the patient's body is imaged on a position on the x-ray detector 3b indicated by a cross. Since the properties of the x-ray imaging system 3 are known, a spatial axis A can be determined, for example relative to the viewing direction of the x-ray imaging system 3, on which the point C must lie. However, the location of the point C along the spatial axis A cannot be determined from the output of the x-ray detector 3b.

In order to determine the location of the point C along the spatial axis A, the pixel in the output image of the detector 4b of the x-ray imaging system 4 which images the point C has to be identified. Since the point C must lie on the spatial axis A, the pixel which images the point C must lie on a line in the output image of the detector 4b which is the projection of the spatial axis A into the imaging plane of the detector 4b. This line is referred to as epipolar line and indicated by E in FIG. 2.

In the present exemplary embodiment, the point C is the center of a tumor in the body of the patient P. For a treatment using the radiotherapy system 1, the point C must lie on the treatment beam of the treatment beam generator 2. Preferably, the point C lies in the isocenter of the radiotherapy system 1.

Figure 3:
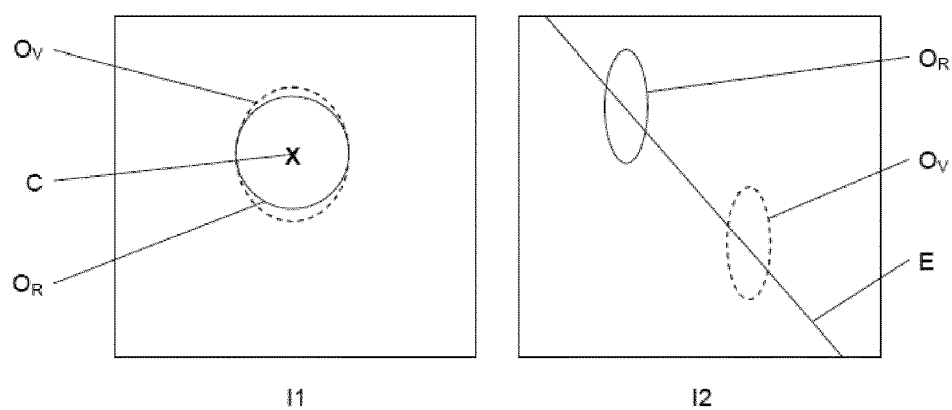

FIG. 3 schematically shows the two 2D images generated by the x-ray imaging systems 3 and 4. The 2D image I1 is the output image of the detector 3b and the 2D image I2 is the output image of the detector 4b. While the output images of the detectors 3b, 4b are typically grayscale images, the output images I1 and I2 shown in FIG. 3 only comprise the contours of an object $O_R$ in the body of the patient P. The contour of the object $O_R$ is indicated by a solid line.

Figure 4:
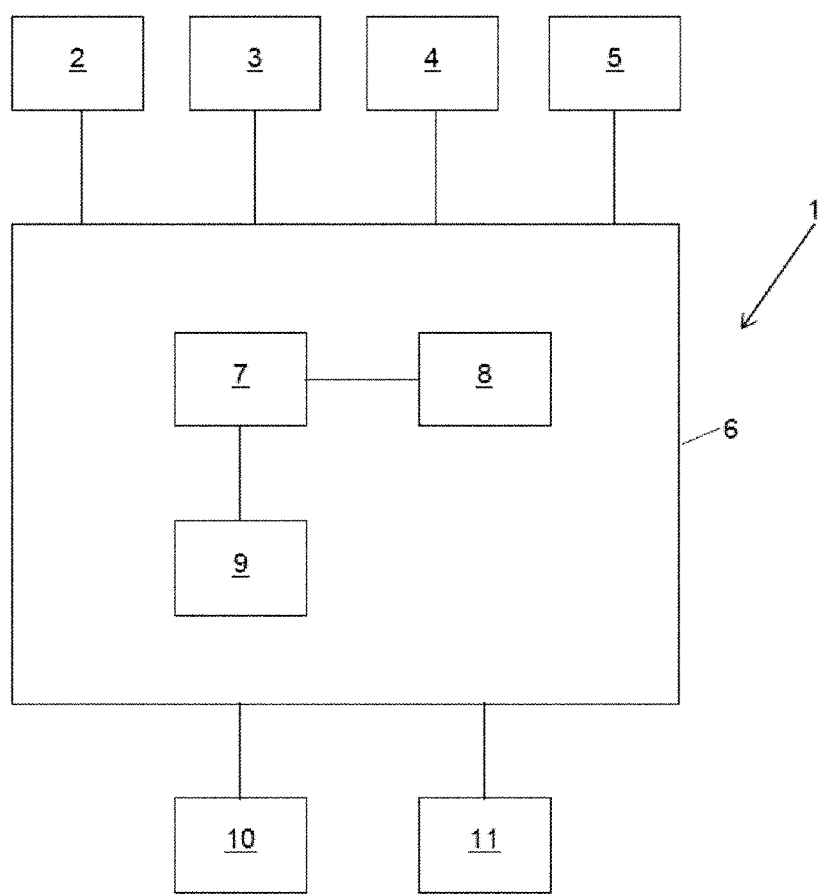

FIG. 4 schematically shows a data processing structure of the system 1. It comprises a computer 6 being connected to or a part of the system 1. The computer 6 comprises a central processing unit 7, a memory unit 8 and an interface unit 9. Via the interface unit 9, the computer 6 is connected to the treatment beam generator 2, the x-ray imaging units 3 and 4 and the couch 5. The interface unit 9 can also be used to obtain the 3D image data, for example from a storage unit or a 3D imaging system. The memory unit 8 stores working data, such as 3D image data of at least a part of a patient's body and the 2D images captured by the x-ray imaging units 3 and 4, and a computer program which instructs the central processing unit 7 to perform the method described herein.

Connected to the computer 6 is an input unit for receiving user input, such as a keyboard, a mouse, a touch sensitive surface or the like. The computer 6 is further connected to an output unit 11, such as a display unit, which can for example display the images I1 and I2 shown in FIG. 3.

The computer 6 receives 3D image data which represent at least a part of a patient's body and, in the present case, represent at least a part of at least one bone, which is subsequently referred to as bone structure, and a tumor $O_R$. As an optional step, the computer 6 performs an initial fusion. This involves acquiring two initial 2D images from the x-ray imaging systems 3 and 4 and performing an initial fusion step of the 3D image data with the two initial 2D images based on the bone structure represented by the 3D image data and the bone structure as it is represented in the initial 2D images. The result of the initial fusion is an initial virtual position of the 3D image data relative to the x-ray imaging units 3 and 4. The location of the center C of the tumor $O_R$ in the 3D image data relative to the treatment beam generator 2 can be calculated from the initial virtual position of the 3D image data. If the point C does not lie in the isocenter of the treatment beam generator 2, the computer can issue a positioning command to the couch 5 to reposition the patient P such that the location of the point C and the isocenter of the treatment beam generator 2 coincide.

After the initial fusion, the virtual position of the bone structure in the 3D image data equals the real position of the corresponding bone structure in the patient P. However, the position of the tumor in the patient P and the virtual position of the tumor in the 3D image data might differ because the tumor has moved within the body of the patient P. So even if the patient P is correctly positioned relative to the treatment beam generator 2, it might be necessary to identify the actual position of the tumor relative to the treatment beam generator 2.

As explained above, the principle of a fusion of 3D image data with a 2D image captured by an imaging system is to virtually arrange the 3D image data relative to the imaging system such that a virtual image calculated from the 3D image data and assuming a virtual imaging system having the same properties and the same position as the real imaging system matches the 2D image as good as possible. For two or more 2D images, a joint optimization of the virtual position of the 3D image data is calculated. The result of the fusion is therefore a virtual position of the 3D image data in space. The position is typically given by three rotational components and three translational components, such that the fusion is also referred to as 6D fusion.

The central processing unit 7 acquires the 3D image data, for example from the memory unit 8 or an external 3D imaging system (not shown). It further acquires two 2D images from the imaging units 3 and 4 or the memory unit 8.

The central processing unit 7 calculates two virtual images from the 3D image data, the two virtual images corresponding to the two 2D images captured by x-ray imaging units 3 and 4, respectively. The virtual images are for example calculated for an initial virtual position of the 3D image data in space, such as the initial virtual position calculated during an initial fusion or assumed from a proper position of the patient P.

The central processing unit then classifies the two 2D images into a primary and a secondary image. Assuming the two 2D images shown in FIG. 3, the primary image is the image I1 and the secondary image is the image I2. The primary image I1 is the image in which the visibility of the tumor $O_R$ is higher than in the other image I2. Different approaches for classifying the 2D images into a primary and a secondary image are described elsewhere in this document. The virtual image corresponding to the primary image I1 is referred to as primary virtual image, and the virtual image corresponding to the secondary image I2 is referred to as secondary virtual image.

The central processing unit 7 then determines a primary alignment between the primary image and the primary virtual image. In this exemplary embodiment, this in particular involves to shift the primary virtual image relative to the virtual image in the imaging plane such that the tumor as shown in the primary virtual image matches the tumor as shown in the primary image as good as possible. In the primary image I1 shown in FIG. 3, the contour of the tumor is indicated as a solid line and labeled $O_R$. The contour of the tumor in the virtual image is overlaid over the primary image I1 and shown as a dashed line labeled $O_V$.

The central processing unit 7 then calculates a spatial axis A relative to the viewing directions of the two 2D images captured by the x-ray imaging systems 3 and 4 from the primary alignment and a predetermined point which is imaged in the primary virtual image. In this exemplary embodiment, the predetermined point is the point C, which is the center of the tumor. The location of the point C in the virtual image is known since the location of the point C in the 3D image data is known. The primary alignment therefore defines the pixel of the primary image by which the point C is imaged. The central processing unit 7 then calculates the spatial axis A from the location of the said pixel in the primary image I1 and the properties of the x-ray imaging system 3. The primary alignment then defines two translational components of the virtual position of the 3D image data in space in translational directions which are perpendicular to the spatial axis A. The only translational component not yet known is the component along the spatial axis A. This information can be used to reduce the (computational) complexity of a subsequent fusion step described below.

The central processing unit 7 then performs a fusion of the 3D image data with the two 2D images based on the calculated spatial axis in order to obtain the virtual position of the 3D image data in space. This fusion can be an automatic fusion or a manual fusion. It can be limited to calculating the missing translational component of the virtual position of the 3D image data or may further involve to also calculate the orientation of the 3D image data in up to three rotational dimensions.

In a first exemplary embodiment, the fusion is a manual fusion. In this exemplary embodiment, the primary alignment was for example determined manually by receiving user input via the input unit 10, wherein the user input effected the shift of the primary virtual image relative to the primary image I1.

The central processing unit 7 then calculates a projection of the spatial axis A into the imaging plane of the detector 4b. It then receives user input via the input unit 10 for shifting the secondary virtual image relative to the secondary image I2 until the contour $O_R$ of the tumor in the secondary image I2 and the contour $O_V$ of the tumor in the secondary virtual image match. However, the user cannot shift the virtual image freely relative to the secondary image I2, but only along the epipolar line E. The epipolar line E can optionally be overlaid over the secondary image i2 to provide the user with additional information.

The display on the output unit 11 is for example updated when user input for manually aligning the secondary image I2 and the secondary virtual image is received. If the secondary virtual image is shifted relative to the secondary image I2, this means a virtual shift of the 3D image data along the spatial axis A. This does, however, mean a change in size of the tumor in the primary virtual image, such that it might be advantageous to update the overlay of the primary image I1 and the primary virtual image by an updated primary virtual image.

The user might optionally be given the opportunity to input a rotation command via the input unit 10. This rotation command performs a virtual rotation of the 3D image data, thus changing the rotational components of the virtual position of the 3D image data.

In another exemplary embodiment, the fusion is an automatic fusion. In one implementation, the automatic fusion is similar to the manual fusion, but instead of receiving user input for shifting the secondary virtual image along the epipolar line, the secondary alignment is calculated automatically by finding the best match. The primary alignment can be calculated automatically rather than being input by a user.

Instead of shifting the secondary virtual image relative to the secondary image I2 along the epipolar line E like in the manual fusion, the central processing unit 7 may shift the 3D image data virtually along the spatial axis A. The central processing unit 7 then calculates the location along the spatial axis A by determining the location for which two virtual images jointly match the two 2D images best. In one implementation, a plurality of locations along the spatial axis A are tested and a pair of virtual images is calculated for each of the those locations. A joint similarity measure value describing the similarity between each of the pairs of virtual images and the two tested 2D images is calculated and the location which results in the highest similarity measure value is selected as the last translational component of the virtual position of the 3D image data.

In another implementation, the fusion is not strictly limited to a location along the spatial axis A (or the epipolar line E), but allows a certain deviation therefrom if this optimizes the fusion result, that is the match between the two virtual images and the two 2D images. However, a deviation from the spatial axis A might be limited by penalizing such a deviation or using a relatively large step width when the one or two component(s) of the virtual position in directions perpendicular to the spatial axis A are tested as explained above.

Irrespective of the type of fusion, that is partly manual or automatic, an offset can be calculated between an initial virtual position of the 3D image data, such as the virtual position obtained by an initial fusion, and the virtual position of the 3D image data after the fusion. This offset is for example indicative of a movement of the object within the patient's body. This offset can then be used for checking the virtual position of the 3D image data for plausibility.

The central processing unit 7 does for example decompose the offset into components along (for translational components) and around (for rotational components) predetermined body axes, such as the superior-inferior-axis, the anterior-posterior-axis and the lateral axis. Depending on the position of the object in the patient's body, certain offsets are plausible and other offsets are not. A breathing activity of the patient P might for example cause a movement mainly along the superior-inferior-axis and hardly along the lateral axis. If, however, the translational component of the offset in the lateral direction is larger than the component in the other two translational directions, then the central processing unit 7 might indicate a warning that the virtual position of the 3D image data obtained by the fusion step is not plausible.

The decomposition can also be applied in an automatic fusion in which deviations from the spatial axis A are penalized. The penalties are then defined with respect to the body axes, which means the patient reference, rather than with respect to the spatial axis A and axes perpendicular thereto. The penalties are thus given in physiologically defined directions. Penalties are for example larger in directions in which a movement of an object is expected than in directions in which such a movement is not expected. The penalties can for example be determined based on object information, such as the position of a tumor within the patient's body. More particular, an offset which defines the deviation of the virtual location of the 3D image data from the spatial axis A is decomposed into components along the body axes and a penalty is applied to a similarity measure value depending on the components or the ratios of the components.

The principle of the present invention can also be applied for tracking an object, such as a tumor, in a sequence of pairs of 2D images. However, instead of performing a full fusion step, a simplified approach can be applied.

In this simplified approach, the object is tracked in the 2D images only. The parts of an initial primary image and an initial secondary image which show the object are used as templates which are searched for in subsequent pairs of 2D images. In this approach, too, the template is first searched for in the primary image in order to calculate an epipolar line for the secondary image along which the corresponding template is to be searched. The templates can also be generated from the virtual images rather than from the initial 2D images.

The invention claimed is:

1. A computer implemented method for performing fusion of 3D image data with two 2D images, comprising:
   acquiring 3D image data representing a part of a patient's body;
   acquiring two 2D images representing the same part of the patient's body;
   calculating two virtual images from the 3D image data, the two virtual images corresponding to the two 2D images;
   classifying the two 2D images into a primary and a secondary image;
   determining a primary alignment between the primary image and the corresponding virtual image so they substantially match;
   calculating a spatial axis relative to the viewing directions of the two 2D images from the primary alignment and a predetermined point which is imaged in the virtual image which corresponds to the primary image, wherein the spatial axis is a line in space on which the predetermined point lies; and
   performing fusion of the 3D image data with the two 2D images based on the calculated spatial axis in order to obtain a virtual position of the 3D image data in space;
   wherein the fusion of the 3D image data with the two 2D images includes at least one of a manual fusion, a partly manual fusion, an automatic fusion, or includes a translational shift of the 3D image along the spatial axis;
   generating positioning commands based on the virtual position of the 3D image data to modify the relative position between a treatment beam generator and the patient.

2. The method of claim 1, wherein the classifying step depends on the visibility of an object in the two 2D images.

3. The method of claim 2, wherein the classification is based on at least one of histograms of the two 2D images and the structure of the 3D image data along rays used for calculating the virtual images corresponding to the two 2D images.

4. The method claim 1, wherein the fusion step involves a partly manual fusion comprising the steps of:
projecting the spatial axis into the secondary image in order to obtain an epipolar line in the secondary image;
receiving user input for manually aligning the secondary image and the corresponding virtual image along the epipolar line only, obtaining a secondary alignment; and
obtaining the virtual position of the 3D image data from the first alignment and the second alignment.

5. The method of claim 4, further comprising the step of displaying an overlay of the primary image with the corresponding virtual image according to the primary alignment and an overlay of the secondary image with the corresponding virtual image according to the secondary alignment.

6. The method of claim 1, wherein performing fusion of the 3D image data with the two 2D images based on the calculated spatial axis includes an automatic fusion which allows a translational shift of the 3D image data only along the spatial axis, wherein the shift is defined with respect to an initial virtual position of the 3D image data.

7. The method of claim 1, wherein performing fusion of the 3D image data with the two 2D images based on the calculated spatial axis includes a translational shift of the 3D image data along the spatial axis being penalized less than a translational shift of the 3D image data in a direction perpendicular to the spatial axis, wherein the shift is defined with respect to an initial virtual position of the 3D image data.

8. The method of claim 1, wherein performing fusion of the 3D image data with the two 2D images based on the calculated spatial axis includes a translational shift of the 3D image data along the spatial axis having a step width which is smaller than a step width of a translational shift of the 3D image data in a direction perpendicular to the spatial axis, wherein the shift is defined with respect to an initial virtual position of the 3D image data.

9. The method of claim 1, wherein the 3D image data represent an object in or on the patient's body and the predetermined point is a point in the object.

10. The method of claim 9, further comprising the step of calculating an offset which represents the difference between an initial virtual position of the object before the fusion and the virtual position of the object after the fusion.

11. The method of claim 10, further comprising the steps of dividing the offset into components along and/or around body axes of the patient and of comparing at least one of the components with a reference value.

12. The method of claim 9, further comprising tracking of the object by repeating the steps of acquiring the two 2D images, calculating a primary alignment, calculating a spatial axis and performing fusion.

13. The method of claim 12, wherein the two 2D images are captured consecutively with the primary image being captured before the secondary image.

14. A non-transitory program stored on a computer readable medium which, when running on at least one processor, causes the at least one processor to:
acquire 3D image data representing a part of a patient's body;
acquire two 2D images representing the same part of the patient's body;
determine two virtual images from the 3D image data, the two virtual images corresponding to the two 2D images;
classify the two 2D images into a primary and a secondary image;
determine a primary alignment between the primary image and the corresponding virtual image so they substantially match;
determine a spatial axis relative to the viewing directions of the two 2D images from the primary alignment and a predetermined point which is imaged in the virtual image which corresponds to the primary image, wherein the spatial axis is a line in space on which the predetermined point lies; and
perform fusion of the 3D image data with the two 2D images based on the calculated spatial axis in order to obtain a virtual position of the 3D image data in space, wherein the fusion of the 3D image data with the two 2D images involves a partly manual fusion;
wherein the fusion of the 3D image data with the two 2D images includes at least one of a manual fusion, a partly manual fusion, an automatic fusion, or includes a translational shift of the 3D image along the spatial axis;
generate positioning commands based on the virtual position of the 3D image data to modify the relative position between a treatment beam generator and the patient.

15. A system for performing fusion of 3D image data with two 2D images, comprising:
at least one imaging system to capture the two 2D images representing the same part of a patient's body as represented in the 3D image data;
at least one processor with associated memory, the memory storing instruction which, when executed by the at least one processor, cause the at least one processor to:
acquire, by the at least one processor, the 3D image data;
acquire, by the at least one processor, the two 2D images;
determine, by the at least one processor, two virtual images from the 3D image data, the two virtual images corresponding to the two 2D images;
classify, by the at least one processor, the two 2D images into a primary and a secondary image;
determine, by the at least one processor, a primary alignment between the primary image and the corresponding virtual image so they substantially match;
determine, by the at least one processor, a spatial axis relative to the viewing directions of the two 2D images from the primary alignment and a predetermined point which is imaged in the virtual image which corresponds to the primary image, wherein the spatial axis is a line in space on which the predetermined point lies; and
perform, by the at least one processor, fusion of the 3D image data with the two 2D images based on the calculated spatial axis in order to obtain a virtual position of the 3D image data in space;
wherein the fusion of the 3D image data with the two 2D images includes at least one of a manual fusion, a partly manual fusion, an automatic fusion, or includes a translational shift of the 3D image along the spatial axis.

16. The system of claim 15, wherein when the at least one processor performs the fusion, the instructions further causing the at least one processor to:
project the spatial axis into the secondary image on order to obtain an epipolar line in the secondary image;
receive user input for manually aligning the secondary image and the corresponding virtual image along the epipolar line only, obtaining a secondary alignment; and obtain the virtual position of the 3D image data from the first alignment and the second alignment.

17. The system of claim 15 further including instructions which, when executed by the at least one processor, cause the at least one processor to generate positioning commands based on the virtual position of the 3D image data to modify the relative position between a treatment beam generator and the patient.

* * * * *